United States Patent [19]

De Simone et al.

[11] Patent Number: 5,719,192
[45] Date of Patent: Feb. 17, 1998

[54] USE OF TERBINAFINE FOR THE THERAPEUTIC TREATMENT OF PNEUMOCYSTOSIS

[75] Inventors: Claudio De Simone, Ardea; Carlo Contini; Sonia Tzoutzoglou, both of Rome, all of Italy

[73] Assignee: Mendes s.r.l., Rome, Italy

[21] Appl. No.: 525,526

[22] PCT Filed: Mar. 11, 1994

[86] PCT No.: PCT/IT94/00023

§ 371 Date: Sep. 12, 1995

§ 102(e) Date: Sep. 12, 1995

[87] PCT Pub. No.: WO94/20082

PCT Pub. Date: Sep. 15, 1994

[30] Foreign Application Priority Data

Mar. 12, 1993 [IT] Italy .................. RM93A0154

[51] Int. Cl.⁶ .................. A61K 31/135; A61K 31/505; A61K 31/42; A61K 31/155

[52] U.S. Cl. .................. 514/655; 514/24; 514/45; 514/275; 514/311; 514/380; 514/564; 514/592; 514/636; 514/646

[58] Field of Search .................. 514/655, 275, 514/311, 380, 564, 636, 646, 592, 24, 45

[56] References Cited

FOREIGN PATENT DOCUMENTS 2 256 139  12/1992  United Kingdom.

*Primary Examiner*—Phyllis G. Spivack
*Attorney, Agent, or Firm*—Evenson, McKeown, Edwards & Lenahan, P.L.L.C.

[57] ABSTRACT

A method of use comprising administering terbinafine for the primary and secondary prophylaxis and treatment of *Pneumocystis carinii* pneumonia, including oral administration of terbinafine at does of 3 to 20 mg/kg/day, to a subject suffering from this type of pneumonia is disclosed.

3 Claims, No Drawings

USE OF TERBINAFINE FOR THE THERAPEUTIC TREATMENT OF PNEUMOCYSTOSIS

This is a 371 of PCT/IT94/00023 filed Mar. 11, 1994.

This invention relates to a new therapeutic use for terbinafine [(E)-N-(6,6-dimethyl-2-hepten-4-inyl)-N-methyl-1-naphthalene-methanamine]. More precisely, this invention relates to the use of terbinafine for the therapeutic treatment of *Pneumocystis carinii* pneumonia, or pneumocystosis.

*Pneumocystis carinii* pneumonia is one of the diseases most frequently encountered in new-born, undernourished children and subjects with leukaemia or lymphoma, as well as in transplant recipients or in patients subjected to immunosuppressive therapy. In addition, it is the most frequent infection and the main cause of death in patients suffering from AIDS.

Treatment is of fundamental importance because the uncured disease carries a very high mortality rate, bordering upon 100%. When promptly treated, pneumocystosis has a 25 to 20% mortality rate (first episode), but relapses are frequent (35% with 6 month, 60% within 12 month) and are associated with a 50 to 60% mortality rate. The mean life expectancy has been calculated as 12,5 months from occurrence of the first episode in U.K. and 9 months in the U.S.A.

The main anti-Pneumocystis drugs in current use are trimethoprim-sulphamethoxazole (cotrimoxazole), pentamidine isethionate, dapsone, the trimethoprim-dapsone combination, trimethotrexate, eflornithine hydrochloride and the clindamycin-primaquine combination. Other drugs can be used such as inosine analogues, dapsone derivatives and carbutamide.

Cotrimoxazole is used at dosage of 20 mg/kg/day i.v. or per os in divided doses every 8 h for 3 weeks (blood concentration 22 5/100 ng/ml). Side effects may occur due to idiosyncratic phenomena and include: skin rash, erythroderma, Stevens-Johnson syndrome, exfoliative dermatitis, fever, anaemia, leukopenia, thrombocytopenia, anorexia, nausea, vomiting, serum creatinine elevation, interstitial nephritis, etc.

Pentamidine is administered at doses of 4 mg/kg/day i.v. for 3 weeks or i.m. (the latter route may cause sterile abscesses). The main side effects are hypoglycaemia, tachycardia, arterial hypotension, shock, serum creatinine elevation, serum transaminase elevation, hallucinations, taste disorders, nausea, vomiting, diarrhoea skin rash, leukopenia and thrombocytopenia.

Pentamidine can also be used by aerosol in both the primary and secondary prophylaxis of *P. carinii* pneumonia. In this case, it reaches high concentrations in the alveolar spaces (>10-fold) and low blood levels (<10 ng/ml as against 600 ng/ml by the hepatic route). No haematic side effects are observed with this administration method. However, cough, bronchospasm, relapses in the upper lobes, and pneumothorax may occur. The drug is administered at the does of 300 mg every d30 days.

Other drugs which can be used for prophylactic purposes are oral cotrimoxazole (160/800 mg b.i.d.) continuously or on three consecutive days each week and Fansidar (1 tablet a week), though the results obtained to date with the latter drug are contradictory.

Other treatments are oral trimethoprim-dapsone (20/100 mg/kg/day) in a once-daily dose for 21 days. The main contraindications are glucose 6-phospate dehydrogenase deficiency and simultaneous intake of zidovudine.

Therapies which are rarely used are those based on trimethotrexate (30/60 mg/m$^2$ i.v.)+leucovorin (20/80 mg/m$^2$ i.m. or per os). Skin rashes or haematological abnormalities may occur. Eflornithine (100 mg/kg i.v. every 6 h) can cause reduced Hb, thrombocytopenia, skin rash and nausea.

The combination of clindamycin and primaquine (900 mg of clindamycin i.v. every 8 h+30 mg of primaquine/day) can give rise to nausea, haematological abnormalities or altered liver function parameters.

During the acute phase of pneumocystosis, corticosteroids can be administered, which are thought to exert a certain limiting action on mononuclear infiltrates and on type 2 alveolar cell hyperplasia. In addition, they are thought to inhibit the action of phospholipase A (surfactant degradation).

To date, terbinafine has been used exclusively in the treatment of superficial mycoses. The knowledge acquired regarding terbinafine seems so far to exclude its use for the treatment of *P. carinii* pneumonia (Balfour J. A., Faulds D. Terbinafine: E. R. review of its pharmacodynamic and pharmacokinetic properties and therapeutic potential in superficial mycoses. Drugs, 43: 259–284, 1992). Moreover, attempts to use it in the treatment of deep-seated mycosis have failed according to the findings reported in studies conducted in pulmonary aspergillosis and in cryptococcosis (Haueser M, Schmitt H J, Bernard E M, Armstrong D. A. new bioassay for Terbinafine: Eur. J. Clin. Microbiol. Infect. Dis., 7: 531–538, 1988; Polak A., Discon D. M. Chemotherapeutic activity in a mouse model of cryptococcosis with cutaneous and nasal involvement: Mycoses, 31: 501–507, 1988; Schmitt H. J., Andrade J., Edwards F. et al. Inactivity of terbinafine in a rat model of pulmonary aspergillosis. Eur. J. Microbiol. Infect. Dis., 9: 832–835, 1990). On the basis of these data, terbinafine could not have been regarded as effective for the treatment either of deep-seated mycotic infections of the immunodepressed host or of pneumocystosis.

Surprisingly, however, it has now been found that terbinafine, at oral doses ranging from 3 to 20 mg/kg/day is potentially effective for the prophylaxis and treatment of *P. carinii* infections in transplant recipients, cancer patients or undernourished subjects and in patients with acquired immunodeficiency syndrome (AIDS) or with immunodeficiency secondary to treatments with immunosuppressive agent or to radiation therapies.

This efficacy of terbinafine has been tested in various studies both in animals and in man. A number of these studies are described here below. Furthermore, the administration of terbinafine at the doses indicated above does not cause any of the previously mentioned toxic or unwanted side effects.

ANIMAL STUDY

A study was conducted aimed at assessing the efficacy of terbinafine in preventing *P. carinii* infections in rates treated with corticosteroids.

Two batches (A and B) were considered, both consisting of 31 Sprague-Dowley rats weighing 180–200 g. Each rat was subjected to immuno-suppressive treatment with cortisone acetate (25 mg/kg s.c.) and to a low-protein (8%) diet for 12 weeks. From week 4 on, the batch A rats were treated with oral terbinafine in addition to the cortisone treatment; the batch B rats, on the other hand, were administered cortisone acetate alone until sacrificed. Body weight was measured for each rat at weekly intervals. At the end of week 12, all rats were sacrificed and lungs, after being removed aseptically, were stored at –70° C. until used. For each lung, in addition to histological preparations to isolate bacteria and fungi, slides were also prepared for application of lung tissue for *P. carinii*-specific cytological staining (Giemsa and Gomori-grocott). Portions of lung tissue were also triturated, homogenized in HBSS (Hank's balanced salt solution) and digested with collagenase and hyaluronidase. The material thus obtained was washed repeatedly, re-suspended in HBSS and subject to immunocytochemical staining (immunofluorescence with *P. carinii* monoclonal antibodies). The results obtained are given in the following table.

liver and pancreatic function tests, serum LDH assay, etc.). In patients on prophylaxis with trimethoprim-sulphamethoxazole, no alterations were detected in the radiological picture and no evidence was found for presence of *P. carinii* in induced sputum. Of the 3 patients on pentamidine prophylaxis, 1 showed intolerance of the drug around treatment week 12, whereas the other 2 presented repeated evidence of presence of *P. carinii* in inducted sputum. At radiology, these patients exhibited diffuse accentuation of the pulmonary tissue in the absence of clinical

TABLE

Results obtained with the use of a combination of terbinafine and corticosteroids vs corticosteroids alone in rat batches A and B

| Rats (batch) | Treatment given | Treatment duration | | *P. carinii* | | Degree of infection | Weight reduction | | Died during treatment | |
|---|---|---|---|---|---|---|---|---|---|---|
| | | No. | (weeks) | No. | % | | No. | % | No. | % |
| A | corticosteroids + terbinafine | 31 | 12 | 1 | 3.2 | ++ | 0 | — | 0 | — |
| B | corticosteroids | 31 | 12 | 18 | 58 | ++++ | 23 | 74.1 | 5 | 12.1 |

Five rats (12.1%) in batch B died in the course of weeks 7 and 8, and in none of these cases was the present of *P. carinii* detected in the various suitably treated and stained portions of lung tissue. In the latter, however, numerous Gram-positive and Gram-negative organisms were isolated. In the remaining rats in this batch, *P. carinii* was found in 18 cases (58%), and each lung section exhibited widespread infiltration (20–30 cysts per field) of Pneumocystis.

Weight reductions ranging from 120 to 160 g were found in comparison to baseline.

Among the rats in batch A, *P. carinii* was detected only in 1 (3.2%) and the degree of infection appeared slight (4 to 9 cysts per field). Weight reductions were not observed in any of these rats. None of the batch A rats died.

STUDY IN MAN

The study sample consisted of 7 patients with AIDS and previous *P. carinii* pneumonia (1st episode), 4 of whom (3 males, 1 female, mean age 37 years, all heterosexual) were on secondary prophylaxis with cotrimoxazolo (800 mg of sulphamethoxazole+160 mg of trimethoprim b.i.d. for 3 days) and 3 (1 male, 2 females, mean age 29 years, all i.v. drug abusers) on prophylaxis with pentamidine aerosol (300 mg monthly). All patients presented a number of CD4+ lymphocytes<200 mm$^3$(141±7.9). Each patient was submitted to an 11-month follow-up, during which radiological investigations and an examination of induced sputum were performed at 30-day intervals to detect *P. carinii* so as to assess the efficacy of the treatment. In addition, a number of laboratory parameters were also evaluated (full blood count, signs. On the basis of these data, the three above-mentioned patients agreed to start terbinafine therapy. The drug was administered orally at the dose of 500 mg/day.

Eight months after its initial administration, no idiosyncratic phenomena have been registered and the various laboratory parameters have remained within normal limits, except for a slight elevation of transaminase and LDH values (1 case). Worthy of note are the repeated negative microscopic findings for *P. carinii* in sputum and the normalization of the pulmonary radiological picture throughout the treatment period.

We claim:

1. A method for the primary and secondary prophylaxis and therapeutic treatment of *Pneumocystis carinii* pneumonia comprising administering to a patient terbinafine.

2. A method for the primary and secondary prophylaxis and treatment of *Pneumocystis carinii* pneumonia, which comprises orally administering 3–20 mg/kg/day of terbinafine to a patient suffering from this type of pneumonia.

3. A method for primary and secondary prophylaxis and the therapeutic treatment of *Pneumocystis carinii* pneumonia comprising orally administering terbinafine at doses of 3 to 20 mg/kg/day in combination with trimethoprim-sulphamethoxazole (cotrimoxazole), pentamidine isethionate, dapsone, a combination of trimethoprim and dapsone, trimethotrexate, eflornithine hydrochoride, a combination of clindamycin and primaquine, inosine, or carbutamide.

* * * * *